United States Patent
Varasi et al.

(10) Patent No.: US 6,207,709 B1
(45) Date of Patent: *Mar. 27, 2001

(54) N-SUBSTITUTED-2-AMINO-4-PHENYL-4-OXO-BUTANOIC ACID COMPOUNDS HAVING KYNURENINE-3-HYDROXY BASE INHIBITORY ACTIVITY

(75) Inventors: Mario Varasi, Milan; Antonio Giordani, Pavia; Massimo Cini, Milan; Carmela Speciale, Milan; Alberto Bianchetti, Milan, all of (IT)

(73) Assignee: Pharmacia & Upjohn S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,722
(22) PCT Filed: Jul. 31, 1997
(86) PCT No.: PCT/EP97/04271
§ 371 Date: Feb. 24, 1999
§ 102(e) Date: Feb. 24, 1999
(87) PCT Pub. No.: WO98/09938
PCT Pub. Date: Mar. 12, 1998

(30) Foreign Application Priority Data

Sep. 3, 1996 (GB) .................................................. 9618349

(51) Int. Cl.$^7$ .................................................. A01N 37/12
(52) U.S. Cl. .......................... 514/538; 514/562; 560/12; 562/430; 562/442
(58) Field of Search .................... 562/430, 443, 562/444, 442; 514/562, 567, 563, 533, 534, 538; 560/12, 13, 15, 16, 17, 19; 564/26, 32

(56) References Cited

U.S. PATENT DOCUMENTS 4,758,661 * 7/1988 Melilo et al. .
5,495,044 * 2/1996 Phillips et al. .

FOREIGN PATENT DOCUMENTS

WO95/03271 * 2/1995 (WO) .

OTHER PUBLICATIONS

Sahoo, P S et al. "Inhibition of Matrix Metalloproteinases by N–Carboxyalkyl Dipeptides" Bioorganic & Med. Chem. Lett. vol. 5 No. 20 pp. 2441–2446. See Scheme 1 and Table 1, 1995.*

Yato, M. et al "Reduction of Aromatic Ketones into Methylenes using Triethylsilane and Titanium Tetrachloride. Synethesis of 2–Aminobutanoic Acids" Heterocycles vol. 41 No. 1 pp. 17–20. See Table 1, 1995.*

* cited by examiner

Primary Examiner—Gary Geist
Assistant Examiner—Leigh C. Maier
(74) Attorney, Agent, or Firm—Oblon, Spivak, McClelland, Maier & Neustadt, P.C.

(57) ABSTRACT

An N-substituted-2-amino-4-phenyl-4-oxo-butanoic acid compound of the formula (I):

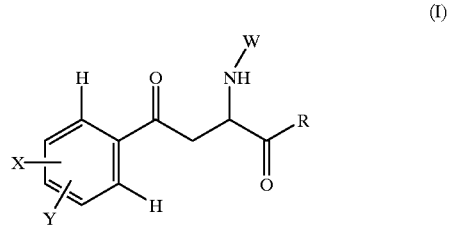

Figure 1:
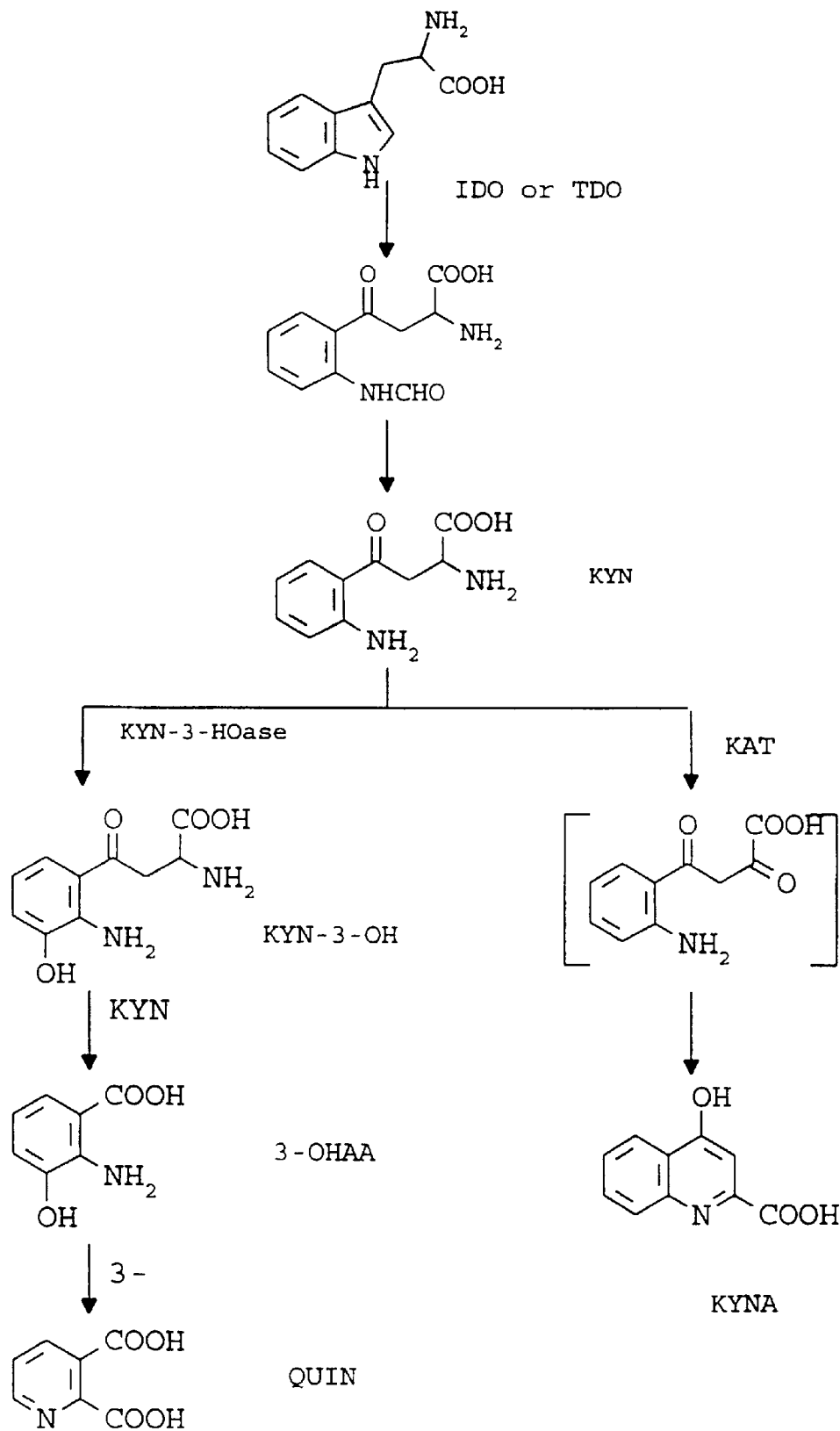

wherein X, Y, W and R are as defined herein.

7 Claims, 1 Drawing Sheet

N-SUBSTITUTED-2-AMINO-4-PHENYL-4-OXO-BUTANOIC ACID COMPOUNDS HAVING KYNURENINE-3-HYDROXY BASE INHIBITORY ACTIVITY

This application is a 371 of PCT/EP97/04271 filed Jul. 31, 1997.

BACKGROUND OF THE INVENTION

1. Field of the Invention

The present invention refers to the use in the prevention and/or treatment of neurodegenerative diseases, such as, for example, Huntington's chorea, Alzheimer's disease, dementia caused by aquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammations of the brain, of N-substituted-2-amino-4-phenyl-4-oxo-butanoic acid derivatives which act as inhibitors of kynurenine-3-hydroxylase (KYN-3-OHase), the enzyme which forms part of the metabolic pathway of kynurenine.

A second object of this invention is directed to a restricted class of the above N-substituted-2-amino-4-oxo-4-phenyl-butanoic acid derivatives as novel compounds, either as single enantiomers or as mixture of enantiomers, to their pharmaceutically acceptable salts, to a process for their preparation, and to pharmaceutical compositions containing them.

2. Description of the Background

In the central nervous system (CNS) the metabolism of tryptophan is well known to result largely in the production of indolamines such as the neurotransmitter serotonin, while in the periphery most of non-peptide tryptophan utilisation is along the kynurenine pathway, ultimately leading to the formation of nicotinamide adenine dinucleotide (NAD) (FIG. 1). The legend to FIG. 1 is to be found on the last page of the experimental part. In the last decade several lines of evidence have demonstrated that two intermediates of the kynurenine metabolism, quinolinic acid (QUIN) and kynurenic acid (KYNA), when injected in the CNS, act as a neurotoxin and as a neuroprotectant, respectively. Consequently, the demonstration that these two metabolites of the kynurenine pathway (unable to cross the blood brain barrier), are normal constituents of the mammalian brain, has suggested the existence of this pathway within the CNS and proposed the involvement of QUIN and KYNA in brain physiology and pathology (Stone T. W., Pharmacol. Rew., (1993), 310–379). Both QUIN and KYNA are able to interact with the ionotropic excitatory amino acid receptors. In particular, QUIN is a highly selective agonist at N-methyl-D-aspartate (NMDA) receptor (Stone T. W., Eur. J. Pharmacol., 72, (1981) 411–412), whereas KYNA is a broad spectrum antagonist of the ionotropic excitatory aminoacid receptors, preferentially acting at the glycine co-agonist site of the NMDA receptor (J. Neurochem., 52, (1989) 1319–1328). In vitro studies have demonstrated that the exposure of neuronal cell cultures to relatively low QUIN concentrations are neurotoxic either when applied over a prolonged period of time or in combination with glutamate (Schurr A., Brain Res., 568, (1991) 199–204). In vivo QUIN has been shown to produce convulsions and axon sparing lesions that mimic the nerve cell loss described in human neurodegenerative disorders (Schwarcz R., Science, 219, (1983) 316–318). Moreover an increase in QUIN production has been demonstrated in post-ischemic gerbil brain (Saito K., J. Neurochem., 60, (1993) 180–192), following spinal cord trauma in rats (Stokes B. T., Brain Res., 633, (1994) 348–352) and in guinea pig (Blight A. R., Brain Res., 632, (1993) 314–316), and, finally, in a model of experimental allergic encephalomyelitis (Flagan E. M., J. Neurochem., 64, (1995) 1192–1196). On the other hand, KYNA has shown anticonvulsant and neuroprotective properties in several animal models (Stone T. W. Pharmacol.Rev.45,(1993) 309–379), and, additionally, the experimentally-evoked rise of KYNA concentrations is capable to elicit neuroprotection and seizures reduction (Nozaki K., J. Cereb. Blood Flow Metab., (1992), 12, 400–407; Russi P., J. Neurochem., 59, (1992) 2076). Notably, KYNA when co-injected with QUIN is able to prevent the excitotoxic neuronal damage evoked by the neurotoxin (Foster A. C., Neurosci. Lett., 48, (1984) 273–278). These data taken together suggest that KYNA may act as the brain's own defence against detrimental events, such as excitotoxicity and seizures, leading to pathological situations (Schwarcz R., Neurotoxin and neurodegenerative disease, Ann. N.Y.Sci., 140, vol. 648, 1992). It follows that pharmacological interventions aimed at increasing KYNA formation and/or blocking QUIN synthesis can be useful in the treatment of excitotoxic brain diseases. In the Kynurenine pathway (see FIG. 1), KYN-3-OHase is the first enzyme involved in the formation of QUIN from kynurenine. Pharmacological agents acting as inhibitors of this enzyme able to block the metabolism toward QUIN and, at the same time, to increase KYNA formation, can be useful as neuroprotective agents in the prevention and/or treatment of all the neurodegenerative pathologies involving quinolinic acid or excessive activation of neurotransmission mediated by excitatory amino acid (EAA) receptors.

There is therefore a need to find pharmacological substances which can be useful as neuroprotective agents by means of their activity as inhibitors of the enzyme KYN-3-OHase. The present invention fulfills such a need.

SUMMARY OF THE INVENTION

Accordingly, the present invention provides a N-substituted-2-amino-4-phenyl-4-oxo-butanoic acid compound of formula (I)

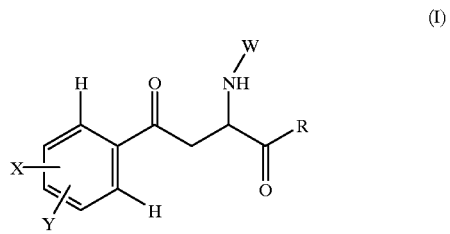

wherein
each of the groups X and Y is, independently, hydrogen; halogen; nitro; $C_1$–$C_6$ alkyl; $C_2$–$C_4$ alkenyl; $C_2$–$C_4$ alkynyl; $C_1$–$C_6$ alkoxy; $C_1$–$C_6$ alkylthio; $SOR_2$ or $SO_2R_2$ in which $R_2$ is $C_1$–$C_6$ alkyl, phenyl or benzyl; or $SO_2N(R_3)_2$ in which each of the groups $R_3$ is, independently, hydrogen, $C_1$–$C_6$ alkyl, $C_2$–$C_4$ alkenyl, $C_2$–$C_4$ alkynyl, phenyl or benzyl;

R is hydroxy; —$OR_5$ in which $R_5$ is $C_1$–$C_6$ alkyl, $C_2$–$C_4$ alkenyl, $C_2$–$C_4$ alkynyl or benzyl; —$N(R_3)_2$ or —$N(R_3)OR_3$ in which each of $R_3$ is as defined above;

w is —$COOR_4$, —$COR_4$ or —$SO_2R_4$ in which $R_4$ is $C_1$–$C_6$ alkyl, an optionally substituted $C_2$–$C_4$ alkenyl, an optionally substituted phenyl or benzyl; —$CONHR_5$ or —CSNHR$_5$ in which R$_5$ is as defined above; trichloroacetyl; or trifluoroacetyl; and the pharmaceutically acceptable salts thereof, for use as a medicament, in particular as Kynurenine 3-hydroxylase inhibitors.

DETAILED DESCRIPTION OF THE PREFERRED EMBODIMENTS

A preferred class of compounds of formula (I) are those wherein each of the groups X and Y is, independently, hydrogen; halogen; nitro; C$_1$–C$_6$ alkyl; C$_1$–C$_6$ alkoxy; C$_1$–C$_6$ alkylthio; SOR$_2$ or SO$_2$R$_2$ in which R$_2$ is C$_1$–C$_6$ alkyl, phenyl or benzyl; SO$_2$N(R$_3$)$_2$ in which each of the groups R$_3$ is, independently, hydrogen, C$_1$–C$_6$ alkyl, C$_2$–C$_4$ alkenyl, C$_2$–C$_4$ alkynyl, optionally substituted phenyl or benzyl;

R is hydroxy;

W is —COOR$_4$, —COR$_4$ or —SO$_2$R$_4$ in which R$_4$ is C$_1$–C$_6$ alkyl, an optionally substituted C$_2$–C$_4$ alkenyl, an optionally substituted phenyl or benzyl, trichloroacetyl or trifluoroacetyl; and the pharmaceutically acceptable salts thereof.

Examples of specific compounds of formula (I) are the following:

N-methylsulfonyl-2-amino-4-oxo-4-(3',4'-dichlorophenyl) butanoic acid;
N-trifluoroacetyl-2-amino-4-oxo-4-(3'-chlorophenyl)-butanoic acid;
N-trifluoroacetyl-2-amino-4-oxo-4-(3'-fluorophenyl)-butanoic acid;
N-trifluoroacetyl-2-amino-4-oxo-4-(3',4'-dichlorophenyl)-butanoic acid;
N-trifluoroacetyl-2-amino-4-oxo-4-(3',4'-difluorophenyl)-butanoic acid;
N-trifluoroacetyl-2-amino-4-oxo-4-(3'-chloro-4'-methoxyphenyl)-butanoic acid;
N-acetyl-2-amino-4-oxo-4-(3',4'-dichlorophenyl)butanoic acid;
N-trifluoroacetyl-2-amino-4-oxo-4-(3'-fluoro-4'-methoxyphenyl)-butanoic acid;
N-benzoyl-2-amino-4-oxo-4-(3',4'-dichlorophenyl)-butanoic acid;
N-methoxycarbonyl-2-amino-4-oxo-4-(3',4'-dichlorophenyl)-butanoic acid;
N-benzyloxycarbonyl-2-amino-4-oxo-4-(3',4'-dichlorophenyl)-butanoic acid; either as single enantiomers or as mixture of enantiomers and the pharmaceutically acceptable salts thereof.

The following compounds of formula (I) either as single enantiomers or as a mixture thereof, and the pharmaceutically acceptable salts thereof are novel compounds and are a further object of this invention:

N-methylsulfonyl-2-amino-4-oxo-4-(3',4'-dichlorophenyl) butanoic acid;
N-trifluoroacetyl-2-amino-4-oxo-4-(3'-chlorophenyl)-butanoic acid;
N-trifluoroacetyl-2-amino-4-oxo-4-(3'-fluorophenyl)-butanoic acid;
N-trifluoroacetyl-2-amino-4-oxo-4-(3'-chloro-4'-methoxyphenyl)-butanoic acid;
N-trifluoroacetyl-2-amino-4-oxo-4-(3'-fluoro-4'-methoxyphenyl)-butanoic acid;
N-benzoyl-2-amino-4-oxo-4-(3',4'-dichlorophenyl)-butanoic acid;
N-methoxycarbonyl-2-amino-4-oxo-4-(3',4'-dichlorophenyl)-butanoic acid; and
N-benzyloxycarbonyl-2-amino-4-oxo-4-(3',4'-dichlorophenyl)-butanoic acid.

The present invention also refers to a selected class of compounds of formula (I) which are novel compounds. Accordingly, a further object of the invention, is a compound of the following formula (Ia)

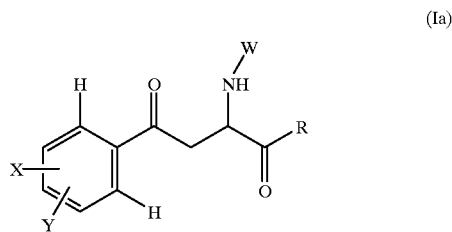

wherein each of the groups X and Y is, independently, hydrogen; halogen; nitro; C$_1$–C$_6$ alkyl; C$_2$–C$_4$ alkenyl; C$_2$–C$_4$ alkynyl; C$_1$–C$_6$ alkoxy; C$_1$–C$_6$ alkylthio; SOR$_2$ or SO$_2$R$_2$ in which R$_2$ is C$_1$–C$_6$ alkyl, phenyl or benzyl; or SO$_2$N(R$_3$)$_2$ in which each of the groups R$_3$ is, independently, hydrogen, C$_1$–C$_6$ alkyl, C$_2$–C$_4$ alkenyl, C$_2$–C$_4$ alkynyl, phenyl or benzyl;

R is hydroxy; —OR$_5$ in which R$_5$ is C$_1$–C$_6$ alkyl, C$_2$–C$_4$ alkenyl, C$_2$–C$_4$ alkynyl or benzyl; —N(R$_3$)$_2$ or —N(R$_3$)OR$_3$ in which each of R$_3$ is as defined above;

W is —SO$_2$R$_4$ in which R$_4$ is C$_1$–C$_6$ alkyl, an optionally substituted C$_2$–C$_4$ alkenyl, an optionally substituted phenyl or benzyl; —CONHR$_5$ or —CSNHR$_5$ in which R$_5$ is as defined above; and the pharmaceutically acceptable salts thereof.

Preferred compounds of formula (Ia) are those wherein W is SO$_2$R$_4$ in which R$_4$ is C$_1$–C$_4$ alkyl and X and Y, which may be the same or different are hydrogen or halogen.

A preferred example of a compound of formula (Ia) is N-methylsulphonyl-2-amino-4-oxo-4-(3',4'-dichlorophenyl) butanoic acid, either as single enantiomer or as a mixture thereof, and the pharmaceutically acceptable salts thereof.

With reference to formula (I) and (Ia), the preferred meanings of the various substituents are as follows.

The alkyl and alkoxy groups may be branched or straight groups.

Representative examples of a C$_1$–C$_6$ alkyl group include methyl, ethyl, n- and iso-propyl, n-, iso-, sec- and tert-butyl.

Representative examples of a C$_1$–C$_6$ alkoxy group include methoxy and ethoxy.

Representative examples of a C$_1$–C$_6$ alkylthio group include methylthio, ethylthio and isopropylthio.

Representative examples of a C$_2$–C$_4$ alkenyl group include ethenyl, 1-propenyl and 2-propenyl.

Representative examples of a C$_2$–C$_4$ alkynyl group include ethinyl, 1-propinyl and 2-propinyl.

A substituted phenyl or benzyl ring is, preferably, a methoxy, a halogen or a nitro substituted phenyl or benzyl ring.

Halogen includes fluoro, bromo, chloro and iodo; in particular fluoro or chloro.

The compounds of formula (I) or (Ia) have an asymmetric carbon atom and, for this reason, they can exist either as a mixture of optical isomers (enantiomeric mixture) or as single optical isomer (enantiomer). The present invention includes within its scope all the possible isomers and their mixtures and both the metabolites and the pharmaceutically acceptable bioprecursors (otherwise known as pro-drugs) of the compounds of formula (I) or (Ia).

The pharmaceutically acceptable salts of the compounds of formula (I) or (Ia) include the salts of inorganic bases, for example hydroxides of alkali metals, e.g. sodium or potassium, or alkaline-heart metals, e.g. calcium or magnesium, and the salts of organic bases such as, for example, aliphatic amines, e.g., methyl amine, ethyl amine or diethyl amine, or heterocyclic amines, e.g. piperidine.

The novel and known compounds of formula (I), the novel chemical entities of formula (I) and the selected class of formula (Ia) included, and the pharmaceutically acceptable salts thereof are therein defined as "the compounds of the invention" and as "the active compounds of the invention".

Object of the invention is also to provide the use of a compound of the invention in the manufacture of a medicament for use as kynurenine-3-hydroxylase inhibitor.

The invention also provides a method of inhibiting kynurenine-3-hydroxylase enzyme in a mammal, including humans, in need of such inhibition, comprising administering to the mammal a kynurenine-3-hydroxylase enzyme-inhibiting effective amount of a compound of the invention or a pharmaceutically acceptable salt thereof.

Most of compounds of the present invention, either as racemic mixture or as pure enantiomers may be prepared in a single step process, following the same procedure described from page 19, line 9, to page 22, of the International Patent Application PCT/WO 95/03271, which is reported in the following Scheme 1.

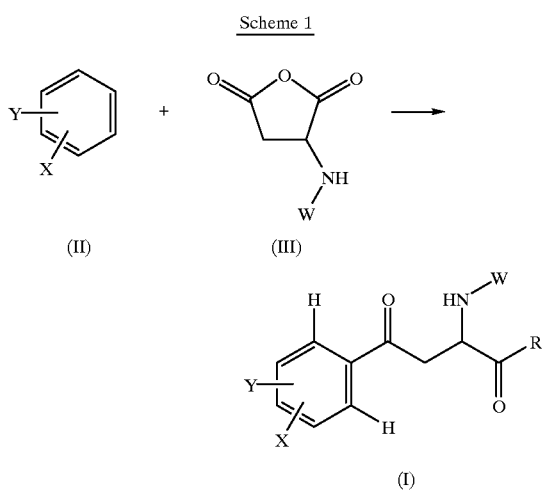

(I)

In the above Scheme 1:

X and Y are, each independently, hydrogen, halogen, $C_1$–$C_6$ alkyl, $C_1$–$C_6$ alkoxy or $C_1$–$C_6$ alkylthio;

R is hydroxy; and

W is —$COOR_4$ or $COR_4$ in which $R_4$ is $C_1$–$C_6$ alkyl, an optionally substituted phenyl or benzyl, or trifluoroacetyl.

A compound of formula (I), obtained following the above procedure, can be converted into another compound of formula (I) in which R is other than hydroxy, according to known methods.

The reaction of a compound of formula (II) with a compound of formula (III), as decribed in Scheme 1, can be carried out according to known methods (e.g. J. E. Norlander, J.Org. Chem., 50, 3619–22, 1985; D. G. Melillo, J.Org. Chem., 52, 5143–50, 1987).

For example, the reaction can be performed in the presence of a suitable Lewis acid catalyst, in an inert solvent such as, e.g. dichloromethane or 1,2-dichloroethane, or in an appropriate aromatic hydrocarbon such as, e.g. chlorobenzene, nitrobenzene or in an excess of compound of formula (II) itself; at a temperature ranging from about −10° C. to about 100° C., optionally in the presence of a suitable co-solvent, e.g. nitromethane. A suitable Lewis acid may be, for example, anhydrous aluminium trichloride, anhydrous tin dichloride, titanium tetrachloride or anhydrous zinc dichloride, typically anhydrous aluminium trichloride.

The compounds of formula (II) are known compounds.

The compounds of formula (III) are known compounds or can be prepared by known procedures from known compounds.

Alternatively, a compound of formula (I) or (Ia) can be obtained according to the following Scheme 2.

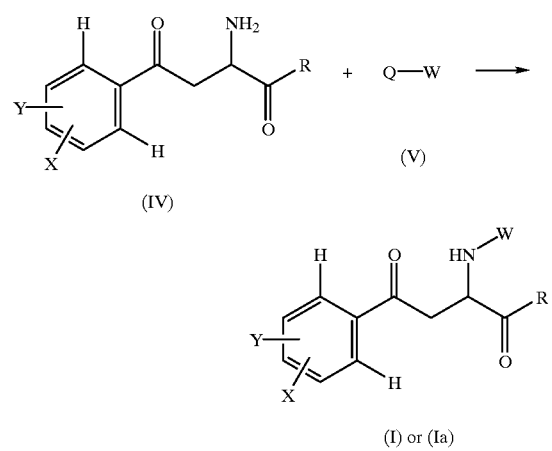

In the above Scheme 2:

each of the groups X and Y is, independently, hydrogen; halogen; nitro; $C_1$–$C_6$ alkyl; $C_2$–$C_4$ alkenyl; $C_2$–$C_4$ alkynyl; $C_1$–$C_6$ alkoxy; $C_1$–$C_6$ alkylthio; $SOR_2$ or $SO_2R_2$ in which $R_2$ is $C_1$–$C_6$ alkyl, phenyl or benzyl; or $SO_2N(R_3)_2$ in which each of the groups $R_3$ is, independently, hydrogen, $C_1$–$C_6$ alkyl, $C_2$–$C_4$ alkenyl, $C_2$–$C_4$ alkynyl, phenyl or benzyl;

R is hydroxy; —$OR_5$ in which $R_5$ is $C_1$–$C_6$ alkyl, $C_2$–$C_4$ alkenyl, $C_2$–$C_4$ alkynyl or benzyl; —$N(R_3)_2$ or —$N(R_3)OR_3$ in which each of $R_3$ is as defined above;

Q is hydroxy; halogen; $R_4COO$— in which $R_4$ is $C_1$–$C_6$ alkyl, an optionally substituted $C_2$–$C_4$ alkenyl, an optionally substituted phenyl or benzyl; trichloroacetoxy; or trifluoroacetoxy; and W is —$COOR_4$, —$COR_4$ or —$SO_2R_4$ in which $R_4$ is as defined above; —$CONHR_5$ or —$CSNHR_5$ in which $R_5$ is as defined above; trichloroacetyl; or trifluoroacetyl.

The compounds of formula (IV) are either known compounds or can be prepared according to known methods from known compounds.

The compounds of formula (V) are commercially available compounds or prepared from commercially available compounds using known methods.

The reaction of a compound of formula (IV) with a compound of formula (V), as decribed in Scheme 2, can be carried out according to methods well known in the art; for example, those usually employed in the synthesis of N-protected aminoacid or of peptides. More in detail, a compound of formula (IV) may be reacted with an acid chloride of formula (V) in the presence of an organic or inorganic base, in a customary organic solvent such as, for example, dichloromethane, tetrahydrofuran or an excess of the base itself (e.g. pyridine).

Other examples of suitable organic bases are triethylamine and N-methylmorpholine, examples of inorganic bases are sodium or potassium carbonate or bicarbonate, in this last case the reaction may be carried out in a two phases system using, if desired, a phase transfer catalyst. The reaction temperature may range from room temperature to about −40° C.

Alternatively, the reaction may be carried out in water using classical Schotten-Bauman conditions at temperature ranging from about 0° C. to room temperature.

A compound of formula (IV) may be reacted with an acid anhydride of formula (V).

A compound of formula (IV) may be reacted with an acid of formula (V) via an intermediate derivative thereof, which can be isolated or not. An intermediate derivative may be an active ester, e.g. a nitro-phenyl ester or an N-hydroxysuccinimide ester, a mixed anhydride, e.g. an ethoxycarbonyl or iso-butyloxycarbonyl anhydride, or a reactive intermediate obtained "in situ" by reaction of the acid with diciclohexylcarbodiimide or carbonyl diimidazole.

For example, an acid of formula (V) and a compound of formula (IV) wherein R is —OR$_5$, —N(R$_3$)$_2$ or —N(R$_3$)OR$_3$ in which R$_5$ and R$_3$ are as defined above, may be reacted with dicyclohexylcarbodiimide, if desired, in the presence of a suitable catalyst (e.g. dimethylaminopyridine or N-hydroxybenzotriazole), in an organic solvent (e.g. dichloromethane), at a temperature ranging from about 0° C. to room temperature.

A compound of formula (I) or (Ia) which contains a free carboxy group, namely a compound of formula (I) or (Ia) in which R is hydroxy, can be converted into another compound of formula (I) or (Ia) in which R is other than hydroxy. This conversion may be carried out according to well known methods. For example, a compound of formula (I) or (Ia) wherein R is hydroxy, can be converted into another compound of formula (I) or (Ia) wherein R is —OR$_5$ in which R$_5$ is as defined above, by usual esterification methods, following the procedure described in: E. Haslam, Tetrahedron, 36, 2409–2433 (1980). Preferably, such an esterification reaction can be carried out via a reactive derivative intermediate of the carboxylic acid , which may be isolated or not, by reaction with the appropriate alcohol of formula R$_5$OH in which R$_5$ is as defined above. The reaction can be carried out in a customary solvent, e.g. dichloromethane, tetrahydrofuran , toluene, or in the presence of an excess of the alcohol itself of formula R$_5$OH, at a temperature which may range from about −20° C. to about 50° C. Intermediate reactive derivatives of the carboxylic acid may be, for example, acid halides, e.g. chloride, mixed anhydrides, e.g. etoxycarbonyl or tert-butyloxy anhydride, or a suitable reactive intermediate obtained "in situ", for example, by reaction with a diimide, e.g. dicychloexylcarbodiimide or carbonyl diimidazole.

The esterification reaction may be also carried out by treatment of a compound of formula (I) or (Ia) in which R is hydroxy, with a suitable alkylating agent of formula R$_5$—L in which R$_5$ is as defined above and L is an appropriate leaving group such as, e.g. a halogen atom, preferably iodine, or a sulfate ester, in the presence of an inorganic base, e.g. potassium carbonate or bicarbonate, or in the presence of an organic base, e.g. 1,8-diazabicyco[5.4.0]-undec-7-ene(1,5-5) (DBU), in a suitable solvent, e.g. dimethylformamide, at a reaction temperature that may range from about 0° C. to about 60° C.

Furthermore, a compound of formula (I) or (Ia) wherein R is hydroxy, can be converted into a corresponding compound of formula (I) or (Ia) wherein R is —N(R$_3$)$_2$ or —N(R$_3$)OR$_3$ werein R$_3$ is, independently, hydrogen, benzyl or C$_1$–C$_6$ alkyl, according to known methods; preferably, via an intermediate reactive derivative thereof, which can be isolated or not. Intermediate derivatives may be active esters, e.g., NO$_2$-phenyl esters or N-hydroxysuccinimide esters, acid halides preferably chlorides, mixed anhydrides, e.g. ethoxycarbonyl or iso-butyloxycarbonyl anhydrides, or reactive intermediates obtained "in situ" by reaction of the acid with diciclohexylcarbodiimide or carbonyl diimidazole.

For example, a reactive intermediate as defined above, which can be obtained following conventional ways, is reacted with ammonia or an appropriate amine HN(R$_6$)$_2$ or an appropriate hydroxylamine or protected hydroxylamine of formula HNO—R$_7$ wherein R$_7$ is a suitable C$_1$–C$_6$ alkyl or benzyl substituent or protecting group; in this last case, R$_7$ is preferably a benzyl or trialkylsilyl group. The reaction solvent may be a customary solvent, such as e.g., dichloromethane, tetrahydrofuran, dioxane or an excess of the amine itself, and the reaction temperature may range from about −20° C. to about 50° C.

The optional salification of a compound of formula (I) or (Ia) as well as the conversion of a salt into the corresponding free compound and the separation of a mixture of isomers into the single isomer, may be carried out by usual methods.

For example, the separation of a mixture of regioisomers obtained as described in Scheme 1, into the single isomer may be carried out by conventional methods. Particularly, the separation of regioisomers may be carried out by fractional crystallization from a suitable solvent or by chromatography, either flash column chromatography or high pressure liquid chromatography.

As previously described, the compounds of formula (I) or (Ia) can exist as enantiomers; the separation of the racemic compounds of formula (I) or (Ia) into the corresponding pure enantiomers can be carried out according to techniques and procedures well known in the art; for example, either high pressure liquid chromatography on a chiral stationary phase, or resolution via diastereoisomeric salt formation of a compound of formula (I) or (Ia) wherein R is hydroxy, with a suitable optically active organic base, e.g., phenylethylamine, ephedrine or brucine, and subsequent separation of the pure diastereoisomeric salt by selective recrystallisation.

It is understood that the preparation of the compounds of formula (I), according to the methods described above, comprises the preparation of the compounds of formula (Ia) which represent a selected class of compounds of formula (I).

Pharmacology

As already said, the compounds of the invention are active as kynurenine-3-hydroxylase inhibitors.

The efficacy of the compounds of the invention in the inhibition of the enzyme kynurenine-3-hydroxylase has been evaluated in rat brain homogenate, determining the conversion of L-kynurenine to L-3-hydroxy-kynurenine according to the method described below.

(A) Kynurenine-3-hydroxylase assay in the rat brain

Brain was homogenized in ice-cold 0.32 M sucrose and centrifuged at 12000×g for 30 min at 4° C. The pellet was washed three times with 0.32 M sucrose by centrifugation and suspended in 0.14 M KCl in 20 mM K-phosphate buffer at pH 7 (1 g tissue in 2 ml buffer).

The reaction mixture contained: 75 µl of suspended homogenate; 100 µl of substrate solution containing 50 mM K-phosphate buffer pH 7.5, 2 mM MgCl$_2$, 0.4 mM NADPH and 50 µM L-kynurenine (final concentration): 25 µl of different concentrations of inhibitor solutions). The reaction was stopped by addition of 200 µl of 1 M HClO$_4$ after 60 min incubation. L-3-hydroxykynurenine formed was quantified by HPLC with coulometric detection at a working voltage of +0.2 V. The column was a 10 cm C$_{18}$ reversed phase (3 µm. The mobile phase consisted of 950 ml distilled water, 20 ml acetonitrile, 9 ml triethylamine, 5.9 ml phosphoric acid, 100 mg sodium EDTA and 1.5 g heptanesulfonic acid. The flow rate was 1 ml/min.

As an example, the compounds of the present invention:

(R,S)-N-trifluoroacetyl-2-amino-4-(3',4'-dichlorophenyl)-4-oxo-butanoic acid (FCE 29256*);
(S)-N-trifluoroacetyl-2-amino-4-(3',4'-dichlorophenyl)-4-oxo-butanoic acid (FCE 29435*); and
(R,S)-N-trifluoroacetyl-2-amino-4-(3',4'-difluorophenyl)-4-oxo-butanoic acid (FCE 29434*);

(* means "Internal Code")

have been tested according to the Method (A) described above.

The obtained results, are reported in the following Table 1.

TABLE 1

| Enzyme Inhibition: Compound | (Rat brain) IC 50 (µM) |
| --- | --- |
| FCE 29256 | 0.14 |
| FCE 29435 | 0.24 |
| FCE 29434 | 0.27 |

The tested compounds, which are representative of the compounds of the invention, were found to be significantly active in inhibiting the enzyme kynurenine-3-hydroxylase.

The compounds of the invention are therefore useful in preventing or treating a disease state in mammals, including humans, wherein inhibition of kynurenine-3-hydroxylase is needed.

In particular, the compounds of the invention can be useful as neuroprotective agents in the prevention and/or treatment of a neurodegenerative disease which comprises: Huntington's chorea, Alzheimer's disease, dementia caused by aquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammation of the brain.

The compounds of the present invention can be administered in a variety of dosage forms, e.g. orally, in the form of tablets, capsules, sugar or film coated tablets, liquid solutions or suspensions; rectally, in the form of suppositories; parenterally, e.g. intramuscolarly or by intravenous injection or infusion.

The dosage level suitable for administration to adult humans depends on the age, weight, conditions of the patient and on the administration route; for example, the dosage adopted for oral administration for the compounds of the invention may range from about 10 to about 500 mg pro dose, from 1 to 5 times daily.

The present invention also provides pharmaceutical compositions comprising a compound of the invention as an active ingredient in association with a pharmaceutically acceptable excipient (which can be a carrier or a diluent).

Furthermore, the present invention provides pharmaceutical compositions comprising a compound of the invention, as an active ingredient, in association with a pharmaceutically acceptable excipient (which can be a carrier or a diluent) for use as kynurenine 3-hydroxylase inhibitor.

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethyl-cellulose, or polyvinyl alcohol.

The suspension or solutions for intramuscolar injections may contain, together with the active compound, a pharmaceutically acceptable carrier, e.g. sterile water, olive oil, ethyl oleate, glycols, e.g. propylene glycol, and, if desidered, a suitable amount of lidocaine hydrochloride. The solutions for intravenous injections or infusions may contain as carrier, for example, sterile water or preferably they may be in the form of sterile, acqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the invention:

EXAMPLE 1

(R,S)-N-trifluoroacetyl-2-amino-4-oxo-4-(3',4'-dichlorophenyl)butanoic acid. (FCE 29256)

To 1,2-dichlorobenzene (60 ml ; 0.53 mol), (R,S)-N-trifluoroacetylaspartic anhydride (20 g ; 0.09 mol) was added in one portion, under dry nitrogen atmosphere at room temperature. To the resulting well stirred suspension, anhydrous aluminium trichloride (36 g.; 0.27 mol) was slowly added portionwise, under dry nitrogen atmosphere, maintaining the temperature below 10° C. The so obtained deep-red solution was stirred at 60° C. for 4 hrs, then cooled at room temperature.

To the resulting reaction mixture, 6N aqueous hydrochloric acid was slowly dropped in, maintaining the temperature below 30° C. on cooling. The so obtained yellow suspension was poured into ice/water (200 g/200 ml), and hexane (200 ml) was added. The resulting suspension was stirred 30 min., then filtered to provide the crude reaction product as slightly yellow solid, which was washed with water and then with hexane, the resulting solid was then dried in a vacuum oven at 50° C.

Recrystallisation from hexane/ethyl ether afforded the pure titled compound as colourless prisms (22 g; 68%), m.p. 172–173° C.

$^1$H-NMR (200 MHz ; d$_6$-DMSO) ppm: 3.60 (d, 2H); 4.78 (d, 1H); 7.79 (d, 1H); 7.90 (dd, 1H); 8.18 (d, 1H); 9.70 (d, 1H), 13.20 (broad s, 1H).

MS (EI; m/z): 357 (M$^+$; 2.5), 304 (12), 173 (100)

Microanalysis: calcd. for $C_{12}H_8Cl_2F_3NO_4$: C 40.26 ; H 2.23; N 3.91; Cl 19.83.

found: 39.53; 2.41; 3.79; Cl 20.17.

Analogously starting from (R,S)-N-trifluoacetylaspartic anhydride the following compounds were obtained:

(R,S)-N-trifluoroacetyl-2-amino-4-oxo-4-(3',4'-difluorophenyl)butanoic acid, (FCE 29434), m.p. 159–160° C.

$^1$H-NMR (200 MHz; d$_6$-DMSO) ppm: 3.58 (d, 2H); 4.78 (m, 1H); 7.60–8.10 (m, 3H); 9.70 (d, 1H), 13.20 (broad s, 1H)

MS (EI; m/z): 325 (M$^+$; 4.5), 307 (55.3), 210 (50), 141 (100)

Microanalysis: calcd. for $C_{12}H_8F_5NO_4$: C 44.35; H 2.45; N 4.35.

found: 44.52; 2.61; 4.08

(R,S)-N-trifluoroacetyl-2-amino-4-oxo-4-(3'-chloro-4'-methoxyphenyl)butanoic acid, (FCE 29573), m.p. 164–65° C.

$^1$H-NMR (200 MHz; d$_6$-DMSO) ppm: 3.58 (m, 2H); 3.96 (s, 3H); 4.78 (m, 1H); 7.30 (d, 1H); 7.98 (d, 1H); 8.0 (s, 1H); 9.70 (d, 1H); 13.10 (broad s, 1H)

MS (EI; m/z): 353.1 (M$^+$; 5), 169.0 (100)

Microanalysis: calcd. for $C_{13}H_{11}ClF_3NO_5$: C 44.16; H 3.13; N 3.96; Cl 10.04.

found: 44.15; 3.22; 3.92; 9.41.

(R,S)-N-trifluoroacetyl-2-amino-4-oxo-4-(3'-fluoro-4'-methoxyphenyl)butanoic acid, (FCE 29574), m.p. 177–78° C.

$^1$H-NMR (200 MHz; d$_6$-DMSO) ppm: 3.53 (m, 2H); 3.92 (s, 3H); 4.78 (m, 1H); 7.30 (t, 1H); 7.72–7.83 (m, 2H); 9.68 (d, 1H); 13.10 (s, 1H)

MS (EI; m/z): 319.0 (8), 153.0 (100)

Microanalysis: calcd. for $C_{13}H_{11}F_4NO_5$: C 46.29 ; H 3.29; N 4.15.

found: 46.52; 3.44; 4.08.

EXAMPLE 2

(S)-N-trifluoroacetyl-2-amino-4-oxo-4-(3',4'-dichlorophenyl)butanoic acid (FCE 29435)

To 1,2-dichlorobenzene (60 ml; 0.53 mol), (S)-N-trifluoroacetylaspartic anhydride (20 g; 0.09 mol) was added in one portion, under dry nitrogen atmosphere at room temperature. To the resulting well stirred suspension, anhydrous aluminium trichloride (36 g.; 0.27 mol) was slowly added portionwise, under dry nitrogen atmosphere, maintaining the temperature below 10° C. The so obtained deep-red solution was stirred at 50° C. for 6 hrs, then cooled at room temperature.

To the resulting reaction mixture, 6N aqueous hydrochloric acid was slowly dropped in, maintaining the temperature below 30° C. on cooling. The so obtained yellow suspension was poured into ice/water (200 g/200 ml), and hexane (200 ml) was added. The resulting suspension was stirred 30 min., then filtered to provide the crude reaction product as slightly yellow solid, which is washed with water and then with hexane, the resulting solid was then dried in a vacuum oven at 50° C.

Recrystallisation from hexane/ethyl ether afforded the pure titled compound as colourless prisms (20 g; 56%), m.p. 154° C.

$[\alpha]_D$=+16.27° (c=1; abs EtOH)

$^1$H-NMR (200 MHz; d$_6$-DMSO) ppm: 3.60 (d, 2H); 4.78 (d, 1H); 7.79 (d, 1H); 7.90 (dd, 1H); 8.18 (d, 1H); 9.70 (d, 1H), 13.20 (broad s, 1H).

MS (EI; m/z): 357 (M$^+$; 2.5), 304 (12), 173 (100)

Microanalysis: calcd. for $C_{12}H_8Cl_2F_3NO_4$: C 40.26; H 2.23; N 3.91; Cl 19.83.

found: 40.66; 2.38; 3.72; Cl 19.68.

Analogously (R)-N-trifluoroacetyl-2-amino-4-oxo-4-(3',4'-dichlorophenyl)butanoic acid was obtained starting from (R)-N-trifluoacetylaspartic anhydride.

m.p. 154° C.

$[\alpha]_D$=−15.1° (c=1; abs. EtOH)

Microanalysis: calcd. for $C_{12}H_8Cl_2F_3NO_4$: C 40.26; H 2.23; N 3.91; Cl 19.83.

found: 40.38; 2.80; 3.22; Cl 18.91.

Analogously starting from the corresponding homochiral N-trifluoacetylaspartic anhydride the following compounds were obtained:

(S)-N-trifluoroacetyl-2-amino-4-oxo-4-(3',4'-difluorophenyl)butanoic acid (FCE 29571); colourless prisms, m.p. 136–137° C.

$[\alpha]_D$=+9.79° (c=0.9; 95% EtOH)

$^1$H-NMR (200 MHz; d$_6$DMSO, ppm): 3.58 (d, 2H); 4.78 (m, 1H); 7.60–8.10 (m, 3H); 9.70 (d, 1H), 13.10 (broad s, 1H)

MS (EI): 325 (M$^+$), 141.0 (100)

Microanalysis: calcd. for $C_{12}H_8F_5NO_4$: C 44.35; H 2.45; N 4.35.

found: 44.20; 2.43; 4.34

(R)-N-trifluoroacetyl-2-amino-4-oxo-4-(3',4'-difluorophenyl)butanoic acid, (FCE 29572), m.p. 136–137° C.

$[\alpha]_D$=−11.4° (c=0.7; 95% EtOH)

Microanalysis: calcd. for $C_{12}H_8F_5NO_4$: C 44.35; H 2.45; N 4.35.

found: 44.43; 2.55; 4.29

EXAMPLE 3

(R,S)-N-benzyloxycarbonyl-2-amino-4-oxo-4-(3',4'-dichlorophenyl)butanoic acid (FCE 29436)

To an ice cooled suspension of (R,S)-2-amino-4-oxo-4-(3',4'-dichlorophenyl) butanoic acid hydrochloride (10 g, 33.5 mmol), in water (70 ml), 1N sodium hydroxide (70 ml, 70 mmol) was dropped in under vigorous stirring. To the resulting solution benzylchloroformate (6.5 ml, 43.5 mmol) and 2N aqueous sodium hydroxyde (23 ml, 46 mmol) were slowly added, from two different dropping funnels, maintaining the reaction temperature below 5° C. The resulting reaction mixture was then stirred at room temperature for two hours, during this time a colourless solid slowly precipitated.

Then the reaction mixture was cooled at 0° C., and on stirring, 2N aqueous hydrochloric acid was slowly added until the pH of the reaction mixture was 2.

The resulting colourless solid was filtered, washed with water and then with hexane, and dried in a vacuum-oven at 60° C.

Recrystallisation of this crude material from ethyl eter/hexane afforded the pure titled compound as colourless prisms (9.5 g, 72% yield), melting at 141–142° C.

$^1$H-NMR (200 MHz; $d_6$-DMSO) ppm: 3.43 (d, 1H); 4.50 (q, 1H); 5.0 (s, 2H); 7.30 (s, 5H); 7.58 (d, 1H); 7.67–7.90 (m, 2H); 8.10 (s, 1H); 12.80 (broad s, 1H)

MS (FAB$^+$; m/z): 396.2 (30); 352.2 (18); 217.4 (100).

Microanalysis: calcd. for $C_{18}H_{15}Cl_2NO_5$: C 54.56; H 3.8; N 3.54; Cl 17.89.

found: 54.68; 3.83; 3.52; 17.97

Using the same procedure the following compounds were obtained:

(R,S)-N-methoxycarbonyl-2-amino-4-oxo-4-(3',4'-dichlorophenyl)butanoic acid (FCE 29593), m.p. 178–180° C.

$^1$H-NMR (200 MHz; $d_6$-DMSO) ppm: 3.42 (d, 2H); 3.56 (s, 3H); 4.50 (q, 1H); 7.43 (d, 1H); 7.80 (d, 1H); 7.92 (dd, 1H), 8.18 (d, 1H); 12.80 (broad s, 1H)

MS (EI; m/z): 319.0 (2); 301.0 (8); 200 (16); 173.0 (100).

Microanalysis: calcd. for $C_{12}H_{10}Cl_2NO_5$: C 45.02; H 3.46; N 4.38; Cl 22.15.

found: 45.06; 3.58; 4.29; 21.95.

(R,S)-N-acetyl-2-amino-4-oxo-4-(3',4'-dichlorophenyl) butanoic acid (FCE 29585), Was obtained with the above reported procedure using $Na_2CO_3$-$NaHCO_3$ buffer instead of NaOH; m.p. 199–203° C. (a first solid-liqid transition was detected by DSC at 190–194° C.).

$^1$H-NMR (200 MHz; $d_6$-DMSO) ppm: 1.80 (s, 3H); 3.42 (d, 2H); 4.65 (q, 1H); 7.79 (d, 1H); 7.90 (d, 1H); 8.13 (s, 1H); 8.16 (d, 1H); 12.65 (broad s, 1H)

Microanalysis: calcd. for $C_{12}H_{10}Cl_2NO_4$: C 47.39; H 3.65; N 4.61; Cl 23.32.

found: 47.38; 3.68; 4.54; 23.21.

(R,S)-N-benzoyl-2-amino-4-oxo-4-(3',4'-dichlorophenyl) butanoic acid (FCE 29584), m.p. 175° C. dec.

$^1$H-NMR (200 MHz; $d_6$-DMSO) ppm: 3.52 (d, 2H); 4.85 (q, 1H); 7.30–7.58 (m, 3H); 7.78–7.82 (m, 3H); 7.90–7.96 (m, 1H); 8.18 (s, 1H); 8.60 (d, 1H).

Microanalysis: calcd. for $C_{17}H_{14}Cl_2NO_4$: C 55.76; H 3.58; N 3.82; Cl 19.36.

found: 53.71; 3.53; 3.70; 20.57.

(R,S)-N-trifluoroacetyl-2-amino-4-oxo-4-(3'-chlorophenyl)-butanoic acid; and (R,S)-N-trifluoroacetyl-2-amino-4-oxo-4-(3'-fluorophenyl)-butanoic acid.

EXAMPLE 4

(R,S)-N-methylsulfonyl-2-amino-4-oxo-4-(3',4'-dichlorophenyl)butanoic acid (FCE 29581)

To a solution of (R,S)-methyl-2-amino-4-oxo-4-(3',4'-dichlorophenyl)butanoate hydrochloride (1.0 g, 3.2 mmol) in dry chloroform (50 ml), cooled at −10° C. and under dry nitrogen atmosphere, triethylamine (0.9 ml, 6.4 mmol) dissolved in dry chloroform (10 ml) was slowly dropped in, keeping the temperature below 0° C. To the stirred resulting suspension, a solution of mesylchloride (0.36 ml, 3.3 mmol) in dry chloroform (10 ml) was added during 15 min., on cooling at 0° C. The resulting yellow reaction mixture was stirred at room temperature further 30 min., and then washed with ice cooled saturated sodium bicarbonate solution, 0.5 N hydrochloric acid solution and then with brine, dried ($Na_2SO_4$) and evaporated under reduced pressure.

The resulting crude material was recrystallised from ethyl ether/hexane to yield (R,S)-methyl-N-methylsulfonyl-2-amino-4-oxo-4-(3',4'-dichlorophenyl)butanoate as colourless needles (g 0.98, 89%), melting at 126–127° C.

$^1$H-NMR (200 MHz; $d_6$-DMSO) ppm: 2.98 (s, 3H); 3.52 (d, 2H); 3.66 (s, 3H); 4.48 (q, 1H); 7.70 (d, 1H); 7.80 (d, 1H); 7.92 (dd, 1H); 8.15 (d, 1H).

To a solution of the above (R,S)-methyl-N-methylsulfonyl-2-amino-4-oxo-4-(3',4'-dichlorophenyl) butanoate (300 mg, 0.84 mmol) in 95% ethanol (20 ml), cooled at 0° C., 1N aqueous sodium hydroxyde solution (1.7 ml, 1.7 mmol) was added.

The resulting reaction mixture was stirred at 0° C. for 3 hours, then neutralised with glacial acetic acid, the most of ethanol was evaporated under reduced pressure, and the residue taken up with ethyl acetate (50 ml), washed with 0.5 N hydrochloric acid and then with brine, dried ($Na_2SO_4$), and evaporated under reduced pressure.

The resulting light yellow solid was recrystallised twice from ethyl ether to provide the pure titled acid as colourless needles (184 mg, 65%), melting at 219° C.

$^1$H-NMR (200 MHz; $d_6$-DMSO) ppm: 2.96 (s, 3H); 3.45 (d, 2H); 4.38 (q, 1H); 7.56 (d, 1H); 7.80–7.95 (m, 2H); 8.08 (s, 1H); 12.95 (broad s, 1H)

MS (FAB$^-$; m/z): 338.3 (80; M+H$^-$); 243.0 (100)

Microanalysis:

calcd. for $C_{11}H_{11}Cl_2NO_5S$: C 38.86; H 3.26; N 4.12; S 9.41; Cl 20.88.

found: 39.51; 3.53; 4.14; 9.33; 20.85.

EXAMPLE 5

(R,S)-methyl-N-trifluoroacetyl-2-amino-4-oxo-4-(3',4'-dichlorophenyl)butanoate (R,S)-N-trifluoroacetyl-2-amino-4-oxo-4-(3',4'-dichlorophenyl)butanoic acid (1.0 g, 2.8 mmol) dissolved in dry methanol (30 ml) was treated at room temperature with 6N methanolic solution of hydrochloric acid (0.9 ml). The resulting solution was warmed on stirring at 40° C. for 4 hrs., then the solvent was distilled off in vacuum, and the residue was taken up with ethyl ether (100 ml); the organic phase was washed with aqueous sodium bicarbonate, then with brine, dried ($Na_2SO_4$), and evaporated under reduced pressure.

The resulting oily material was crystallised with hexane/isopropyl ether to provide the pure titled compound as colourless solid (0.98 g; 96%), melting at 97–98° C.

$^1$H-NMR (200 MHz; $CDCl_3$) ppm: 3.55 (dd, 1H); 3.81 (s, 3H); 3.87 (dd, 1H ); 4.96 (m , 1H); 7.43 (d, 1H); 7.58 (d, 1H); 7.75 (dd, 1H); 8.0 (d, 1H).

MS (EI; m/z): 371 (4); 339 (18); 173 (100).

Microanalysis: calcd. for $C_{13}H_{10}Cl_2 F_3NO_4$: C 41.96; H 2.71; N 3.76; Cl 19.05.

found: 41.83; 2.76; 3.56; 21.03.

EXAMPLE 6

Capsules, each weighing 0.23 g and containing 50 mg of the active substance can be prepared as follows:

Composition for 500 capsules:

| (R,S)-N-trifluoroacetyl-2-amino-4-oxo-4-(3',4'-dichlorophenyl)butanoic acid | 25 g |
|---|---|
| Lactose | 80 g |
| Corn starch | 5 g |
| Magnesium stearate | 5 g |

This formulation can be incapsulated in two hard gelatin capsules of two pieces, each with each capsule weighing 0.23 g.

EXAMPLE 7

Intramuscular injection of 50 mg/ml

A pharmaceutical injectable composition can be manifactured dissolving 50 g of (R,S)-N-trifluoroacetyl-2-amino-4-oxo-4-(3',4'-dichlorophenyl)butanoic acid in sterile propyleneglycol (1000 ml) and sealed in 1–5 ml ampoules.

Legend to FIG. 1, which shows kynurenine pathway
IDO: Indolamineoxygenase
TDO: Tryptophanedioxygenase
KYN: Kynurenine
KYN-3-OHase: Kynurenine-3-hydroxylase
KYN-3-OH: 3-Hydroxy kynurenine
KAT: Kynurenine amino transferase
3-OHAA: 3-Hydroxy anthranilic acid
KYNase: Kynureninase
3-HAO: 3-Hydroxy anthranilic acid dioxygenase
KYNA: Kynurenic acid
QUIN: Quinolinic acid

What is claimed is:

1. A compound of the formula (Ia)

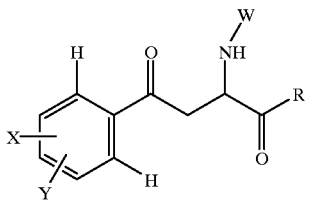

(Ia)

wherein each of the groups X and Y is, independently, hydrogen; halogen; nitro; $C_1$–$C_6$ alkyl; $C_2$–$C_4$ alkenyl; $C_2$–$C_4$ alkynyl; $C_1$–$C_6$ alkoxy; $C_1$–$C_6$ alkylthio; $SOR_2$ or $SO_2R_2$ in which $R_2$ is $C_1$–$C_6$ alkyl, phenyl or benzyl; or $SO_2N(R_3)_2$ in which each of the groups $R_3$ is, independently, hydrogen, $C_1$–$C_6$ alkyl, $C_2$–$C_4$ alkenyl, $C_2$–$C_4$ alkynyl, phenyl or benzyl;

R is hydroxy; —$OR_5$ in which $R_5$ is $C_1$–$C_6$ alkyl, $C_2$–$C_4$ alkenyl, $C_2$–$C_4$ alkynyl or benzyl; —$N(R_3)_2$ or —$N(R_3)OR_3$ in which each of $R_3$ is as defined above;

W is —$SO_2R_4$ in which $R_4$ is $C_1$–$C_6$ alkyl, an optionally substituted $C_2$–$C_4$ alkenyl, an optionally substituted phenyl or benzyl; —$CONHR_5$ or —$CSNHR_5$ in which $R_5$ is as defined above; or a pharmaceutically acceptable salt thereof.

2. The compound of the formula (Ia) according to claim 1 wherein W is $SO_2R_4$ in which $R_4$ is $C_1$–$C_4$ alkyl and X and Y, which may be the same or different are hydrogen or halogen, or a pharmaceutically acceptable salt thereof.

3. The compound of the formula (Ia) according to claim 1 which is N-methylsulphonyl-2-amino-4-oxo-4-(3',4'-dichlorophenyl)butanoic acid, either as single enantiomer or as a mixture thereof, or a pharmaceutically acceptable salt thereof.

4. A method of inhibiting kynurenine-3-hydroxylase enzyme in a mammal in need thereof, comprising administering to said mammal a kynurenine-3-hydroxylase enzyme-inhibiting effective amount of a compound of formula (I) as defined in claim 1, or a pharmaceutically acceptable salt thereof.

5. A pharmaceutical composition for inhibiting kynurenine-3-hydroxylase, which comprises, as an active ingredient, an effective amount of one or more compounds of the formula (I) of claim 1, or a pharmaceutically acceptable salt thereof, in association with a pharmaceutically acceptable carrier.

6. A pharmaceutical composition for inhibiting kynurenine-3-hydroxylase, which comprises, as an active ingredient, an effective amount of one or more compounds of the formula (Ia) of claim 1, or a pharmaceutically acceptable salt thereof, in association with a pharmaceutically acceptable carrier.

7. The method of claim 4, wherein said mammal is a human.

* * * * *